United States Patent [19]

Kaye et al.

[11] Patent Number: 4,576,591

[45] Date of Patent: Mar. 18, 1986

[54] MEDICAMENT IMPLANT APPLICATOR

[75] Inventors: Gordon E. Kaye, Garrison, N.Y.; Eugene B. Schwartz, Altamonte Springs, Fla.; Irving V. Sollins, Jiutepec Morelos, Mexico

[73] Assignee: Ivy-Gene Co., Inc., Overland Park, Kans.

[21] Appl. No.: 597,376

[22] Filed: Apr. 6, 1984

Related U.S. Application Data

[63] Continuation-in-part of Ser. No. 511,251, Jul. 6, 1983, Pat. No. 4,531,938.

[51] Int. Cl.$^4$ .............. A61M 31/00; A61M 5/00; F42B 37/00; B65D 85/24
[52] U.S. Cl. .................... 604/62; 604/57; 604/59; 604/61; 604/208; 604/209; 604/241; 604/343; 206/3; 206/343; 206/528; 206/538; 221/78; 221/79; 221/81; 221/88
[58] Field of Search .............. 221/78, 79, 81, 88; 206/3, 343, 528, 538; 604/57, 59, 61, 62, 63, 64, 208, 209, 241, 343

[56] References Cited

U.S. PATENT DOCUMENTS

| 3,774,607 | 11/1973 | Schmitz | 604/62 X |
| 4,077,406 | 3/1978 | Sandhoge et al. | 604/62 X |
| 4,400,170 | 8/1983 | McNaughton et al. | 604/62 |
| 4,403,610 | 9/1983 | Lodge et al. | 604/61 |
| 4,447,223 | 5/1984 | Kaye et al. | 604/62 X |
| 4,474,572 | 10/1984 | McNaughton et al. | 604/61 |

Primary Examiner—John Doll
Assistant Examiner—William G. Wright
Attorney, Agent, or Firm—Fidelman, Wolffe and Waldron

[57] ABSTRACT

The present invention relates to a pistol grip implanter device adapted for insertion of a solid or semi-solid pellet form medicament into a domestic animal, associated with a hub for an encasement containing a multiplicity of dosage unit pellets of the medicament.

3 Claims, 17 Drawing Figures

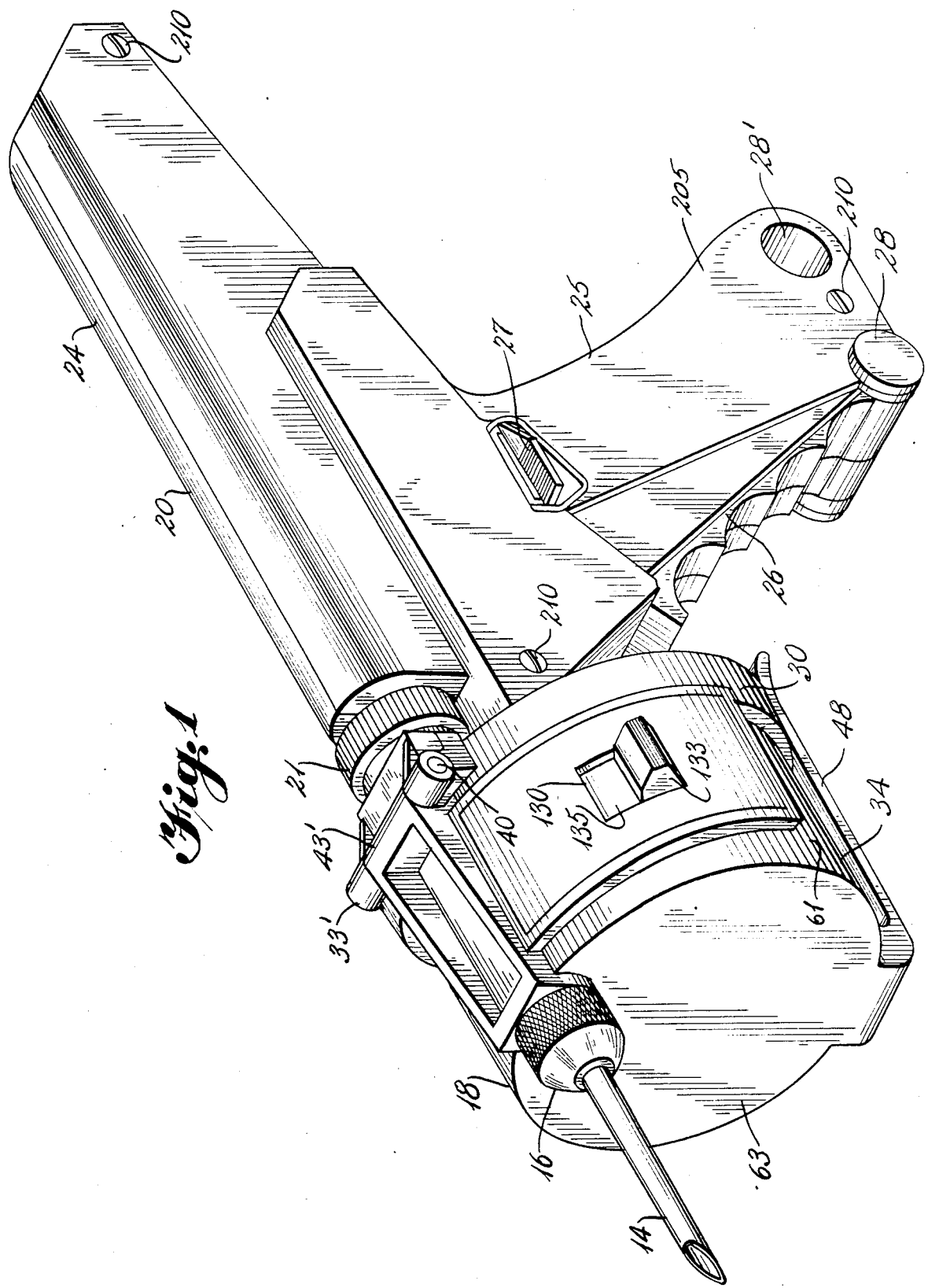

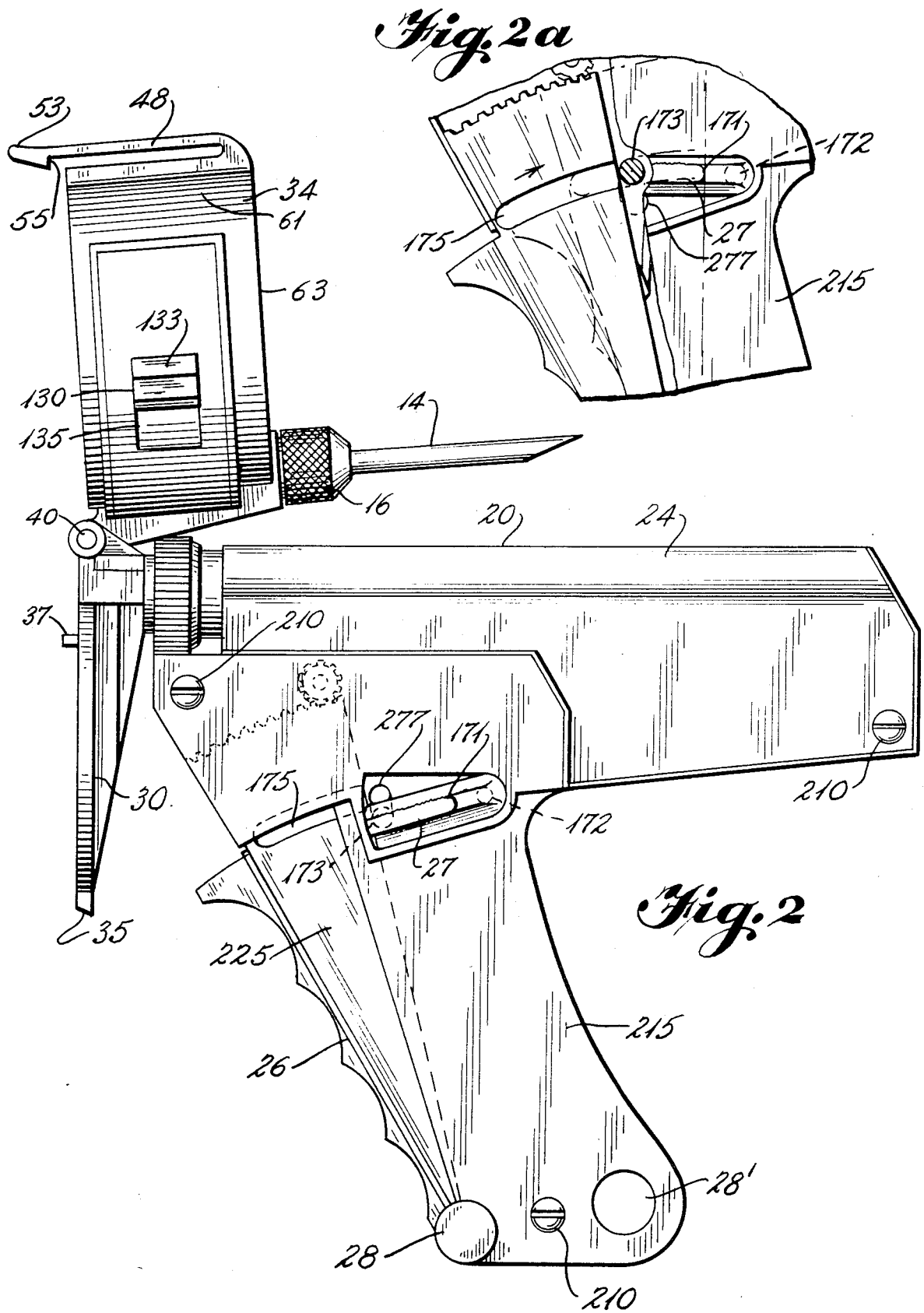

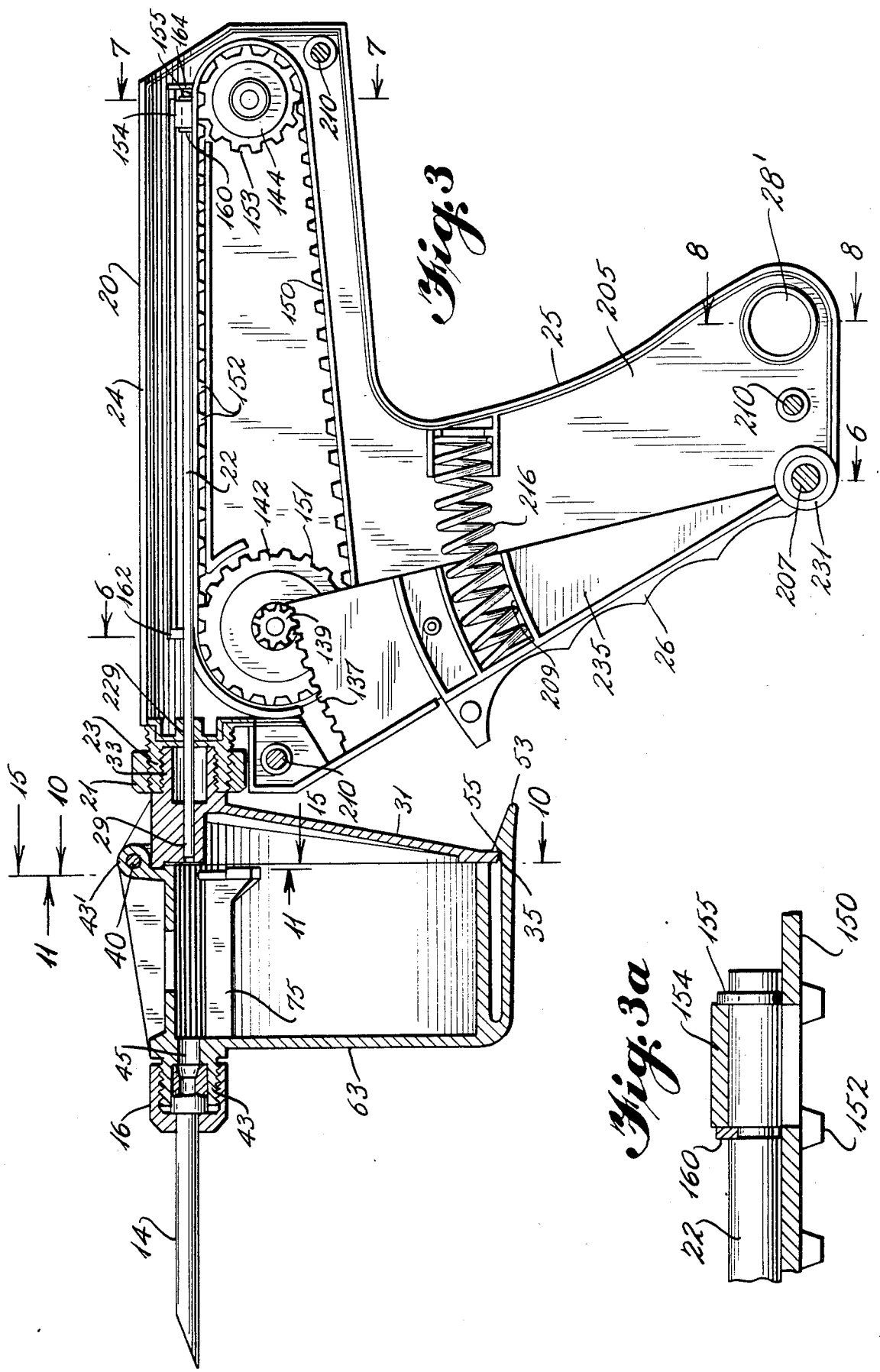

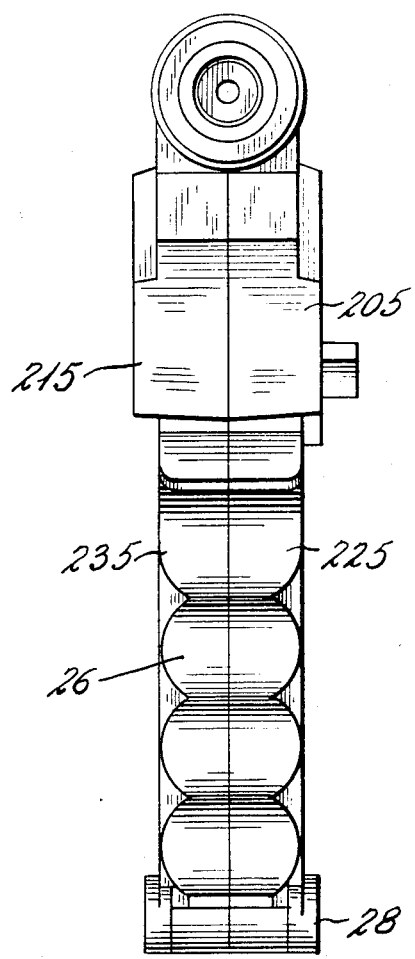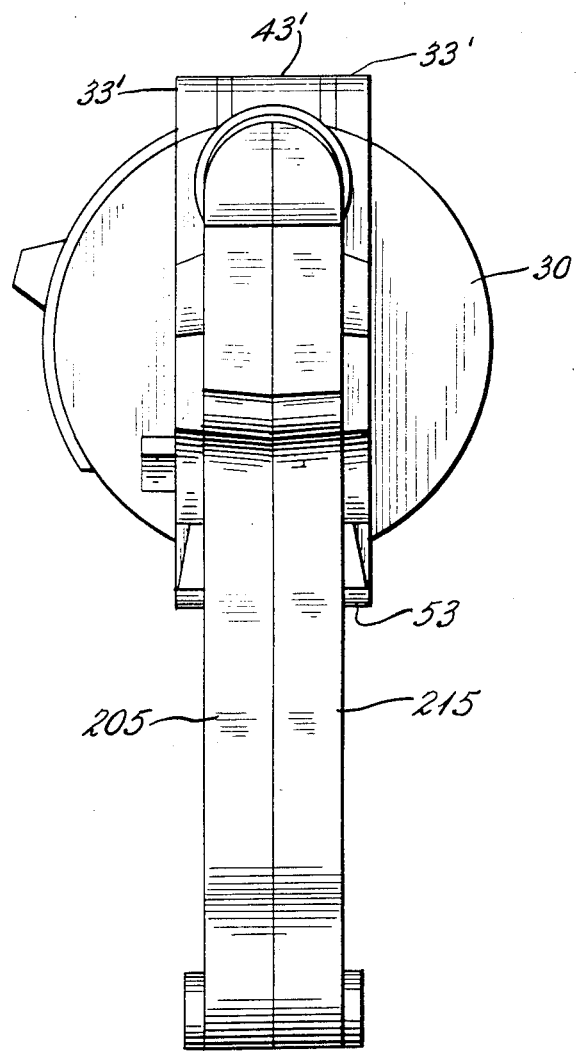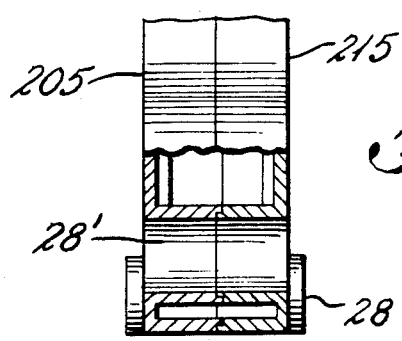

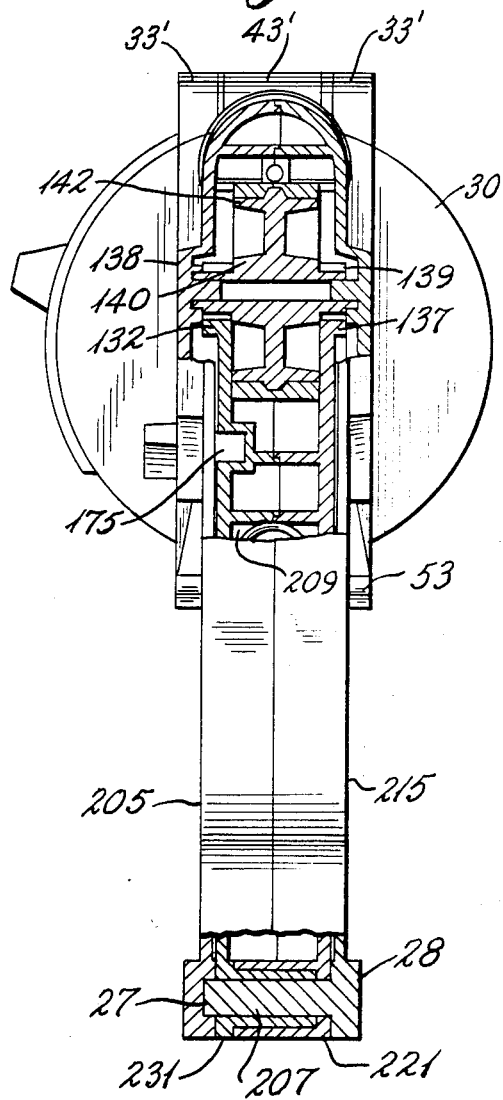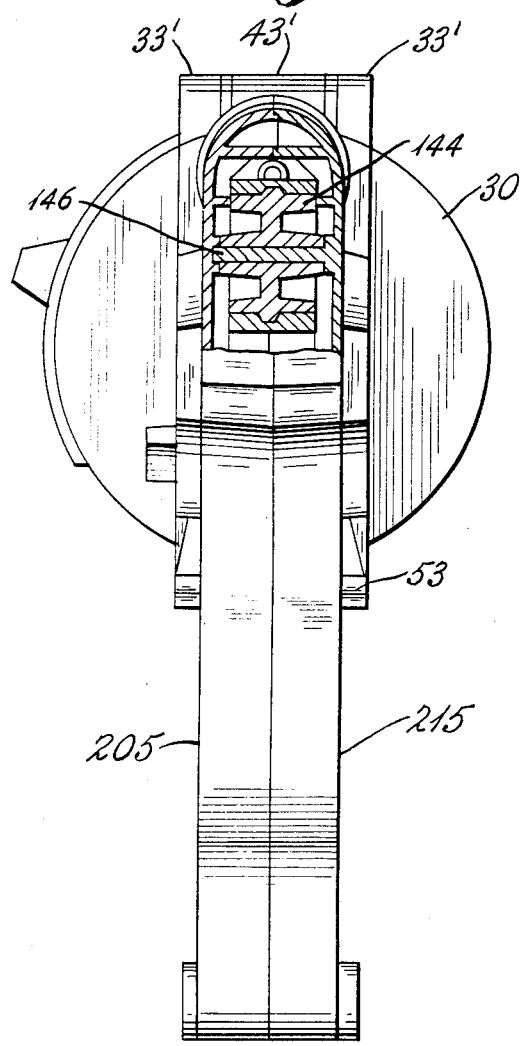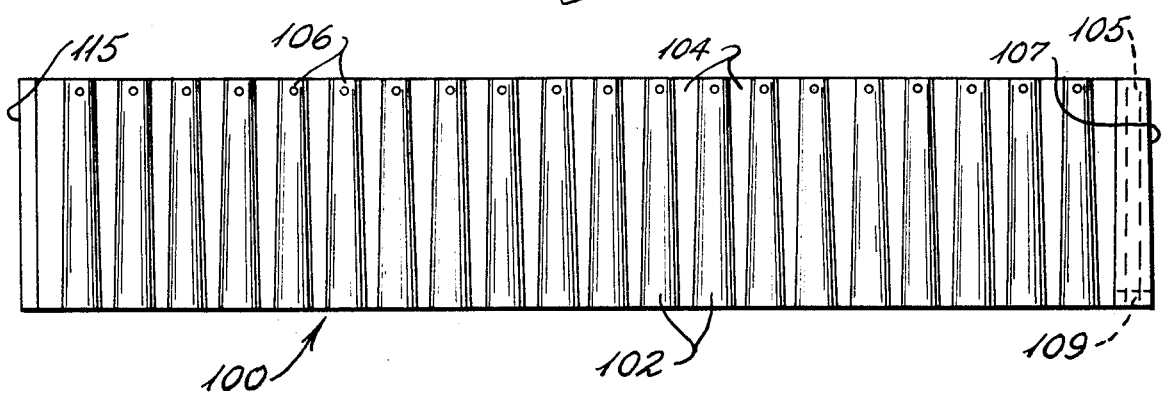

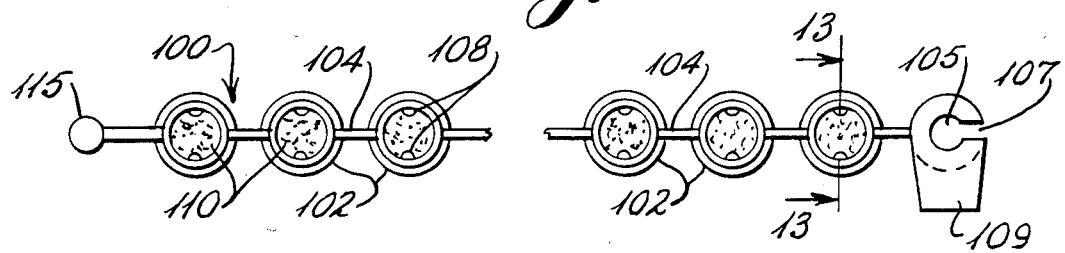
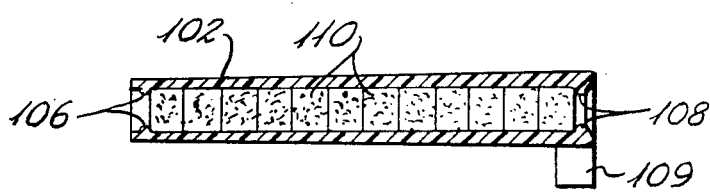
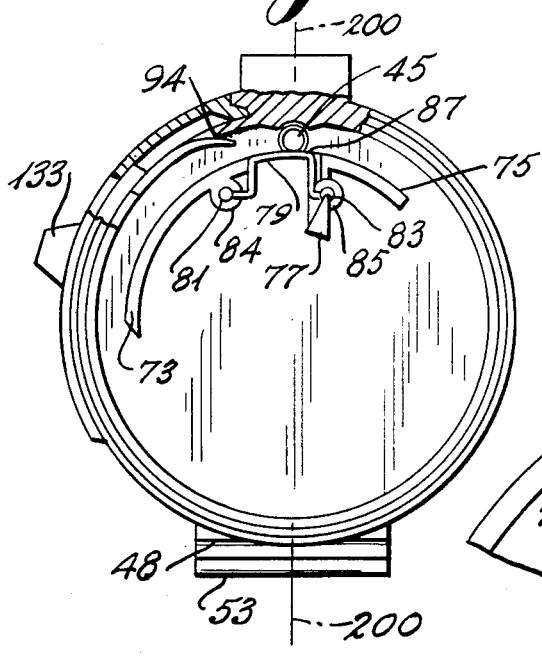
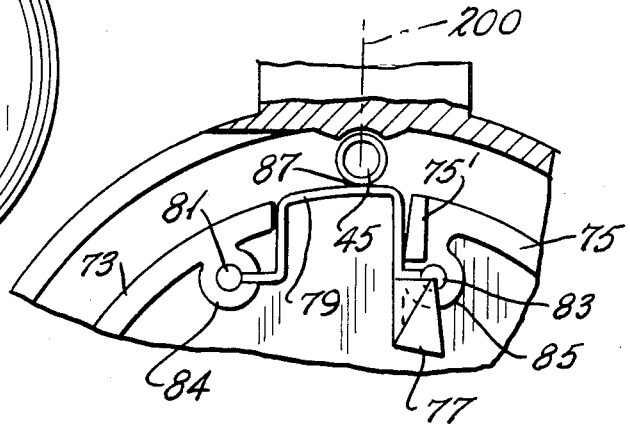

MEDICAMENT IMPLANT APPLICATOR

This is a continuation-in-part of Ser. No. 511,251, filed July 6, 1983, now U.S. Pat. No. 4,531,938.

INTRODUCTION

Good animal husbandry practices sometimes requires insertion into the animal (e.g., intradermally, subcutaneously, intramuscularly, etc.) of a solid or semi-solid medicament. Such practice is common for growth stimulation of cattle, for example. Solid or semi-solid pellets containing the growth stimulating hormones are implanted in the neck or ear of the animal, to remain there for an extended period, even throughout the life span of the animal. The ear is a preferred implantation site, since the ear is a throwaway organ. Any implant residue present in the ear when the animal is slaughtered never enters channels of commerce, to become ingested by people or domestic animals.

A typical medicament implanter device comprises a hand-held instrument built of a size consistent with the size of the animal (large for cattle, small for chickens). An apertured needle on the instrument makes a sizable, non-coring puncture opening into the skin e.g., of the ear of the animal and forms a cavity in the skin occupied temporarily by the needle on the instrument. The body of the instrument may be shaped like a hand gun, or alternatively, like a hypodermic syringe with a receiver-dispenser for the medicament implant. The needle of the implanter is inserted into the skin of the animal, then withdrawn. As the needle is being withdrawn from the animal, pellets of medicament are expelled into the cavity formed by the needle.

For cattle, an implant dosage unit form may constitute a multiplicity, e.g., eight relatively small solid or semi-solid pellets. A reciprocal plunger inside the body of the implanter forces the pellet dosage unit out of a cartridge encasement wherein they were prepackaged into the bore of the needle and from there into the animal.

A number of medicament implant devices have been suggested to the art, including devices adapted for use with cartridges or other encasement forms that contain a multiplicity of dosage units of the implants, U.S. Pat. No. 3,774,607, for example. This invention relates to the multi-dose aspect of the medicament implanter art and, in particular, to the pistol-like devices suggested to this art.

The principal object of the present invention is to provide a novel implant applicator for implantation of the pellets.

The applicator of this invention incorporates features desirable in a multidose applicator, namely, orientation elements that force the user to load the applicator properly and which advise the user when reloading is required. Indeed, the structure of the applicator prevents its use after all the pellets have been discharged from the encasement. Features most desirable to the supplier of the medicament pellets are present. The multidose encasement of this invention may be filled somewhat more readily than single dose cartridges and can be packaged into a most compact form for shipment.

BRIEF DESCRIPTION OF THE APPLICATOR

The pellet implant encasement employed in the applicator of this invention is the same encasement described in parent application, Ser. No. 511,251. The encasement resembles a cartridge belt in appearance. A multiplicity, e.g., 20, of equally spaced apart chambers, are connected in a flexible web. Each chamber is sized to contain therein a dosage unit of medicament, suitably eight pellets. The encasement fits into the applicator of this invention and an animal handler can implant animals in succession, e.g., 20 animals, one after another, from each encasement. Just as the implant encasement is the same as described in parent application, Ser. No. 511,251, so, too, is the storage means for the encasement. It is believed to be a substantial advantage that a major component can be manufactured for use in either the pistol-type implant applicator of this invention or the syringe type implant applicator of parent application, Ser. No. 511,251.

The implant applicator of this invention looks like a pistol constructed with a large hub at the forward end of the pistol barrel. The medicament encasement is loaded inside of the hub; the hub serving as a storage means for the multi-dose medicament encasement. Ahead of the hub is the hollow needle; the plunger is, of course, to the rear of the hub inside the pistol barrel. Forward movement of the plunger expels the implant pellet(s) from one chamber of the encasement into and through the needle at the front end of the applicator. The plunger may be pressed forward as the needle is being withdrawn from an animal into which the needle had previously been inserted, thereby expelling the pellet(s) into the needle track. Later, when the plunger has been retracted fully, the operator of the implanter shifts the encasement the distance between chambers so that a next adjacent chamber in the encasement comes into registry with needle and plunger for expulsion of medicament pellets therefrom by the plunger.

THE IMPLANT APPLICATOR

For further understanding of this invention, reference is now made to the attached drawings wherein:

FIG. 1 is a diagrammatic view of the implant applicator;

FIG. 2 is a side view of the implant applicator showing the applicator in opened position; FIG. 2A is a fragmentary side section illustrating the safety latch structure;

FIG. 3 is a side section of an empty implant applicator showing the applicator in a closed position; FIG. 3A is an enlarged fragmentary side section illustrating attachment of the plunger to the endless drive belt;

FIG. 4 is a front end view of the applicator;

FIG. 5 is a rear end view of the applicator;

FIG. 6 is an end section taken along line 6—6 on FIG. 3;

FIG. 7 is an end section taken along line 7—7 on FIG. 3;

FIG. 8 is an end section taken along line 8—8 on FIG. 3;

FIG. 9 is a plan view of an implant encasement;

FIG. 12 is a side view of an encasement loaded with the medicament pellets;

FIG. 13 is a section taken along line 13—13 on FIG. 12;

FIG. 14 is a rear view similar to FIG. 10 of an empty applicator;

FIG. 15 is an enlarged partial section taken along line 15—15 of FIG. 3.

Figure 10:
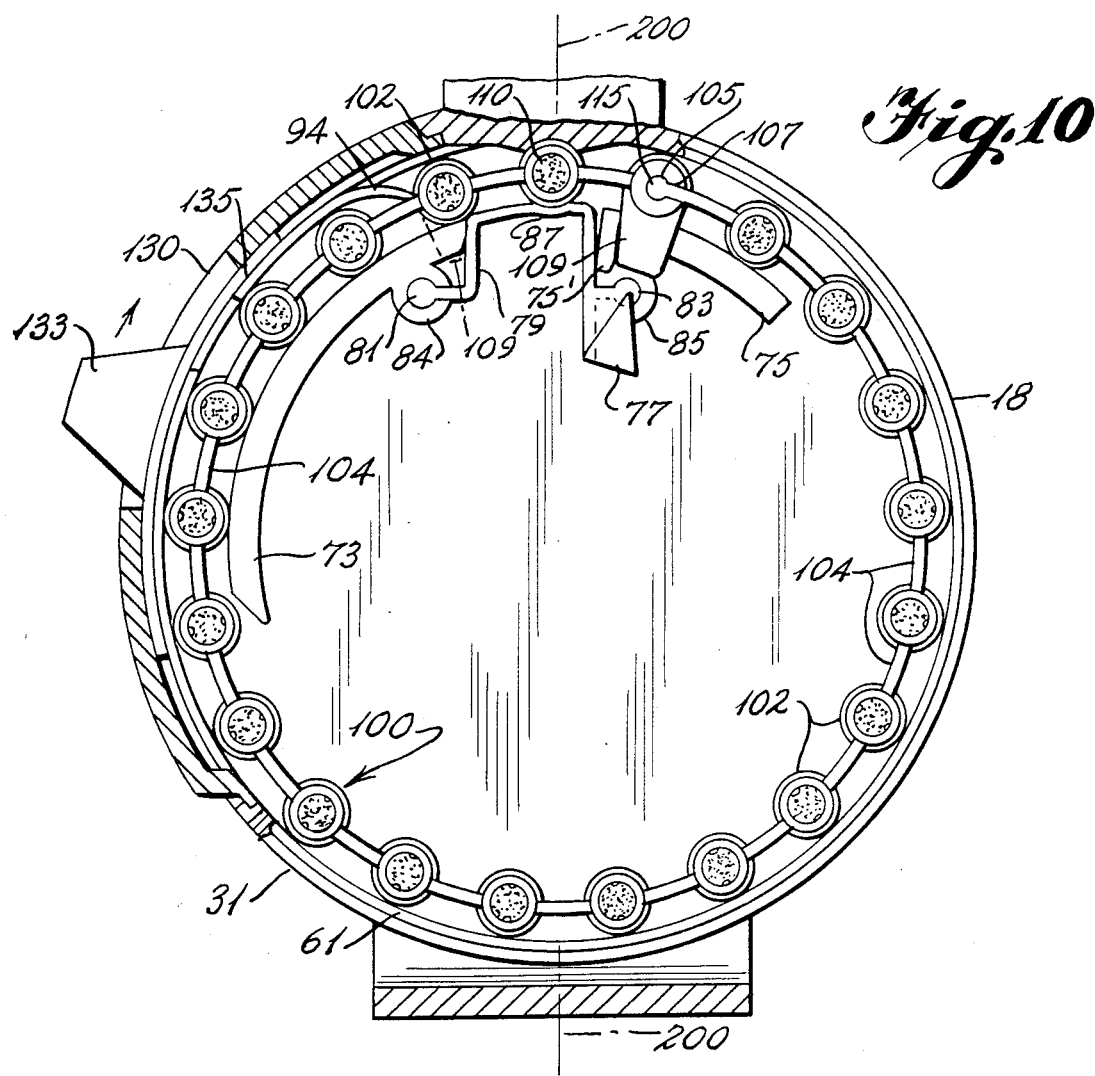
FIG. 10 is a section taken along line 11—11 of FIG. 3 for a loaded implant applicator.

Referring now to the drawing, and in particular to FIGS. 1 and 2, it may be seen that the pistol like implant applicator is a hinged structure split at the hinge into a forward or needle sub-assembly interchangeable with the forward end of the applicator described by patent application, Ser. No. 511,251, and the novel pistol grip and barrel sub-assembly. Thus, the applicator comprises front to rear, left to right on FIG. 1, a hollow needle 14 secured by a chuck 16 (or by any equivalent known to the art mounting structure) to the front of drum 18. Drum 18 contains the medicament encasement therein. To the rear of drum 18 is the pistol grip and barrel 20, which, although a unitary member, will be discussed in terms of barrel portion 24 and pistol grip portion 25.

As best may be seen in FIG. 3, the pistol grip and barrel 20 secured to the rear of drum 18 by nut 21 is aligned to needle 14 so that the concealed plunger 22 shown in FIG. 3 is centered for movement into needle 14 from barrel 24. On the forward side of pistol grip 25 is trigger 26. A safety latch 27 is provided to prevent unintentional pulling of the trigger 26 (see FIGS. 1 and 2). At the forward end of barrel 24 is formed a set of an internally and externally threaded chuck fingers 23 that mount on the threaded boss 33 at the rear of drum 18 to be sandwiched in place by nut 21.

PISTOL GRIP AND BARREL

The basic purpose served by the mechanism inside pistol grip and barrel 20 is, of course, to impel plunger 22 from a retracted rest position just clear of the working parts inside hub 18 to the tip end of needle 14, then to retract plunger 22 to its rest position. The length of the barrel 24 must exceed the travel distance of the plunger. Desirably, the pistol-like implant applicator of this invention, provides a barrel length near to this minimum (see FIG. 3). Thus, the applicator is adapted to be held comfortably by one hand at pistol grip 25 so that the other hand is free to help guide needle 14 into an animal, e.g., subcutaneously.

In its travel, plunger 22 is supported and centered by passageway 29 inside the aforementioned boss 33 on hub 18 and by a passageway 229 at the front of barrel 24. Conveniently, plunger 22 may be metal bar stock cut into desired lengths.

To better understand the invention hereof, the attached drawings omit or partly illustrate, particularly in FIGS. 5–8, some known-to-the-art detail features relating to fabrication of the component parts. For example, the shell of pistol grip and barrel 20 is formed from two casing halves 205 and 215 which are secured together into unitary assembly by screws 210, and such is illustrated, but the drawing should not be considered to have illustrated any exact configuration for the mating edges of 205, 215. Trigger 26 is formed from two trigger halves 225,235 which are joined by matching pin and aperture surfaces thereon, and by a pair of nesting cylindrical portions 221,231 at trigger pivot 28 (see FIG. 6). A hole 28' is provided in pistol grip 25 (see FIG. 8) for the convenience of the user.

Trigger 26, which may be grooved for the user's fingers as illustrated herein, is located at the front of pistol grip 25 and projects out from an opening provided for this purpose between casing halves 205,215. Trigger halves 225,235 are pivotally secured at their nesting cylindrical portions 221,231 at trigger pivot 28 by a pin or shaft 207 and a recess 27 formed respectively in casing halves 215,205 as is illustrated at FIG. 6. The nesting cylindrical portions 221,231 on trigger 26 pivot on pin 207. In addition to the grooved front face and nesting cylinder portions thereof include sector shaped portions extending behind the grooved face from pivot 28 on pistol grip 25 into barrel 24, with a pair of spaced-apart sector gears 132,137 located inside of barrel 24 (see FIGS. 3 and 6) formed at the top edge of the sector portions. A channel 209 is formed in the sector portions of trigger halves 225,235 for seating compression spring 216 behind trigger 26. In the rest position for trigger 26, illustrated by FIG. 3, the front edge of the sectors that is near the sector gears bears against the region of the casing front face adjacent the trigger opening therein.

The sector gears 132,137 on trigger 26 mesh respectively with pinion gears 138,139 on a combination gear 140. The bull gear 142 which also forms part of combination gear 140 is located between the pinion gears 138,139, extending down into the space between the trigger halves 225,235, as may best be seen on FIGS. 3 and 6. When trigger 26 is pulled, spring 216 compresses. In addition, the sector gears 136,137 on trigger 26 move front to rear in the applicator barrel 24 to rotate pinion gears 138,139 counterclockwise rotating as well the bull gear 142 of the combination gear 140. Whenever the pressure on trigger 26 is released, spring 216 expands forcing the trigger to retract (forward) causing the pinion gears and bull gear of combination gear 140 to rotate clockwise.

An endless belt 150, desirably made from a somewhat resilient material such as polyurethane is mounted inside barrel 24 between the bull gear 142 and an idler sprocket 144, the latter being located adjacent the rear of barrel 24. Idler sprocket 144 is rotatably mounted on a shaft 146 formed in casing halve 215. The underside of belt 150 contains a multiplicity of spaced apart teeth 152 that interengage with the recesses between the teeth 151 on bull gear 142 and between teeth 153 of idler sprocket 144, as is illustrated in FIG. 3.

As best seen in FIG. 3A, the plunger 22 is attached at its rear to endless belt 150 by passage through a cutout portion 154 of belt 150 and is retained in place by split lock washers 155,160 that seat in grooves on plunger 22. The plunger 22 which rests atop belt 150 rides forward when belt 150 turns (counterclockwise) on bull gear 142 and sprocket gear 144 as the gears rotate while trigger 26 is being pulled. An exact rectalinear movement for plunger 22 is generated by wall guide surfaces in the spaced apart passageways 29 and 229 through which the plunger travels.

Built into the casing halves 205,215 of the pistol grip and barrel assembly 20 is a forward stop 162 for limiting forward movement of plunger 22 by contact with the retainer ring 160. A rear stop 164 for limiting retraction movement of plunger is also built into casing halves 205,215. Applying the stop action directly on the (metallic) plunger is advantageous since then the resiliency of the material, from which endless belt 150 is formed, can be relied upon to stretch or compress the belt immaterially to compensate for manufacturing tolerances in the applicator components, to absorb acceleration and deceleration forces generated when pulling of trigger 116 impels plunger 22 forward and when retraction of compression spring 216 impels the plunger 22 backward, and to cushion all moving parts in the applicator, should bone or cartilage be encountered inadvertently as pellets are being discharged from the applicator through needle 14.

To prevent inadvertent discharge of the medicament pellets from the applicator, a safety latch 27 has been provided on pistol grip 25 so as to lock trigger 26 in its forward rest position (see FIG. 2). As may be seen in FIGS. 1, 2 and 2A, safety latch 27 comprises a horizontal latch member 171 with a rear pin portion 172 pivotally seated in a recess in casing half 215. On the free forward end of latch member 171 is a retainer button portion 173 that rides in an aperture 277 through casing half 215. In the locked position for the latch 27, the retainer button 173 is positioned directly behind the sector portion of trigger half 225, and contact between button and sector prevents movement by the trigger 26. When the latch member 171 is pivoted into open position, the latch button 173 rides in a longitudinal recess 175 that is provided in trigger half 225 (see FIG. 6) as trigger 26 is being pulled.

Thus, the implant applicator is adapted to be held at pistol grip 25 as firmly as desired (or tied to the user through a string in hole 28) when safety latch 27 is in the locked position. When prior to use, safety latch 27 is pivoted to the operative position, pulling trigger 26 against the force of spring 216 pivots the sector gears 132,137 on trigger 26 toward the rear of pistol grip 25, rotating pinion gears 138,139 and bull gear 142 counterclockwise. In turn, bull gear 142 turns endless belt 150 counterclockwise around bull gear 142 and idler gear 144. The gear ratio of the pinion gears to bull gear 142 are set so that full trigger pull causes just enough movement by endless belt 150 to advance plunger 22 until the forward lock washer 160 reaches stop element 162. The drawings, particularly FIG. 3, are essentially at full scale and illustrate the relationships between the various moving parts of a preferred mode of implant applicator.

At full trigger pull, the forward tip of plunger 22 has advanced through the drum 18 to the front of needle 14, and in doing, has expelled medicament from a medicament encasement disclosed by parent application, Ser. No. 511,251, and described hereinafter for completeness. The drum 18, wherein the medicament encasement is situated, is also disclosed by parent application, Ser. No. 511,251 and is described hereinafter for completeness.

So long as full trigger pull force is applied to trigger 25, plunger 22 will remain in the advanced locale just described, but once the user releases pressure on trigger 26, compression spring 216 expands to force trigger 26 forward, causing reverse movement by sector gears 132,137, rotating pinion gears 138,139 and bull gear 142 clockwise. In turn, bull gear turns belt 150 clockwise to retract plunger 22 to its rest locale. At rest, the rear of plunger 22 is adjacent rear stop 164. At rest, the forward tip of plunger has been withdrawn from needle 14 and drum 18, desirably at or into the passageway 29 that is part of the drum structure, the rest position being illustrated in FIG. 3.

THE DRUM

As has already been pointed out, the purpose of drum 18 is to serve as storage means for a multiplicity of implant dosage units, and to provide means for indexing the stored dosage units one by one in registry with impeller 22 and needle 14.

Mention has already been made that the pistol grip and barrel 20 attach to drum 18 at hub member 30 through the boss 33 thereon. Hub 30, suitably a plastic molding from polyethylene for example, is an integral multipurpose member, with portions thereof being the externally threaded boss 33 and the passageway 29 therethrough for plunger 22. In addition, hub 30 is a separable part of drum 18, being the cover 31 that constitutes the generally circular rear face of drum 18.

As may be seen in FIG. 2, the implant applicator splits at the rear face of drum 18 with hub member 30 to which is attached the pistol grip and barrel assembly 20 pivoting on a hinge 40 away from the rest of drum 18 (and needle 14). At the top of hub 30 is hinge half 33'. As best can be seen in FIG. 3, formed at the bottom of the cover portion 31 of hub member 30 is a detent 35 that serves to latch the cover 31 to the balance of drum 18. Formed on the forward face of hub 30 is an upstanding pin 37 (see FIG. 2) which constitutes a stop element, as will be explained hereinafter.

To repeat, drum 18 is formed from two cooperating separable members, the hub 30 described above and a drum base 34. Like hub 30, the drum base 34 is a multipurpose molded article, from polyethylene for example. At the top of drum base 34 is a hinge-half 43' which mates with hinge-half 33', both halves being mounted on hinge pin 40. When detent 35 at the bottom of cover 31 is released, the drum base 34 and needle 14 of applicator 10 can be pivoted on hinge pin 40 away from cover portion 31 and assembly 20 about 180° to an opened position, as is illustrated in FIG. 2. The inside of drum base 34 is then exposed for loading a fresh medicament encasement therein, as will be explained hereinafter.

At the front of the drum base 34 is an externally threaded boss 43 (see FIG. 2). A passageway 45 in boss 43 is in alignment with the barrel 20 and needle 14. Chuck 16, to which needle 14 is secured, threads onto boss 43. The needle mounting structure comprises known to the art features, which per se, form no part of this invention. Any of the many known equivalent needle mounting structures may be substituted for the arrangement herein illustrated.

Mention has already been made that drum base 34 is formed with the hinge-half 43' at the top thereof. At the bottom of drum base 34 is formed the seat for detent 35, including a detent aperture 55 into which detent 35 seats to latch hub 30 and drum base 34 and releasably permit opening and closing of the applicator. A tab 48 joined to the front of drum base 34 extends front to rear of drum base 34 and beneath detent 35 around to the back of cover 31. By virtue of its length, tab 48 exhibits spring capability so that latch detent 35 can be seated in or released from aperture 55 for closing or opening the applicator by pressing down on the thumb grip 53.

On the whole, drum base 34 looks like an open drum for having a squat cylindrical wall portion 61, and a circular (front) face wall portion 63. Cover portion 31 of hub 30 seats on cylindrical wall 61 to close off the inside of the drum base 34.

For better understanding of the structure present inside of hub 18 for mounting and shifting of the medicament encasement, the structure of the encasement of this invention will be described beforehand.

THE MEDICAMENT ENCASEMENT

Referring now to FIGS. 9, 12 and 13, it may be seen that the medicament encasement 100 resembles a cartridge belt for comprising a series of equally spaced apart parallel cylindrical or conical chambers 102, twenty chambers, for example, connected into a flexible web by web sections 104. Desirably, encasement 100 is a unitary molded article, from polyethylene, for example. For ease of molding, the chambers 102 may be made ever so slightly conical as is herein illustrated (so that the molding equipment releases more readily). If chambers 102 are conical, the larger diameter ends should all be formed at the side of encasement 100 that will be entered by plunger 22. Conical encasement chambers 102 are normally filled from the larger diameter side. The medicament pellets 110 are retained in each chamber 102 by internal tabs 106 molded in the chamber wall adjacent the narrow end of each chamber 102. The tabs 106 reduce chamber clearance to less than diameter of the pellets which causes the pellets 110 to be retained inside chamber 102. Internal tabs 106 may be formed on the inside chamber walls during the molding operation that makes the encasement 100.

Upsets 108 are made in each chamber wall at the wide diameter end of chambers 102 after insertion of the medicament pellets 110 inside chambers 102. Upsets 108 may be formed by the machinery that inserts the medicament pellets inside the chambers. Accordingly, the medicament pellets 110 cannot fall out either end of chamber 102 during later handling of the encasement 100. However, plunger 22 can push the relatively soft medicament pellets 110 past retaining tabs 106 to expel the implant pellet contents from chamber 102.

At one side end of encasement 100 is a dummy chamber 105 that is not intended to be filled with pellets. Optionally, a slot 107 is provided in the end side wall of dummy chamber 105. At the other side end of encasement 100 is a solid cylindrical plug 115 sized-to-fit inside of dummy chamber 105. Slot 107 is sized so plug 115 can be forced through slot 107 into dummy chamber 105. Presence of cylindrical plug 115 and dummy chamber 105 allows encasement 100 to be curved into the circlet mode that is required for use of encasement 100 in the applicator of this invention.

In the circlet mode of encasement 100, presence of plug 115 inside of the dummy chamber 105 helps to block this chamber off against passage by plunger 22; the plunger cannot expel plug 115 from dummy chamber 105. Thus medicament encasement 100 contains a fail-safe feature that advises the user when all the medicament from a particular encasement has been utilized, that time has come to reload the implant applicator.

To facilitate proper orientation of encasement 100 for filling and later for a proper insertion into the implant applicator, an upstanding tab 109 is provided at an end corner of encasement 100, suitably at the dummy chamber 105 end and at the wider diameter, or filling side, of the chamber row, as may best be seen on FIGS. 9 and 13.

Standard filling machinery is adapted to fill a multiplicity of cartridges simultaneously, from a twenty slot filling head for example. Typically, however, separate single dose cartridges have been used for implantation purposes, c.f. U.S. Pat. Nos. 2,761,446 and 3,744,493, requiring then that the multiplicity of separate cartridges be placed into a filling fixture for the filling machine, which, thereafter, allows them to be filled as a single batch. The same filling operation can be done on essentially the same machinery with encasement 100 serving as a filling fixture package for the batch. By placing an indent or slot at the top of a filling fixture that matches tab 109, the tab 109 may be used to orient encasement 100 in a filling fixture for the multislot filling head so that all chambers 102 are filled (from the filling side) simultaneously. Dummy chamber 105 is, of course, not filled. A twenty-unit dosage encasement is somewhat easier to pass into and through conventional filling machinery than twenty separate cartridges.

The multidose package of encasement 100 shown in FIG. 9 is illustrated in flat form, a best form for packaging and shipment. Five or ten encasements stack into a small oblong pack, which may be wrapped as the package form supplied to an ultimate user. An appropriate number of such oblong packs can be boxed together for shipment to a wholesale distributor.

For use in the implant applicator, a circle form is desired. The user curves encasement 100 into a circlet with plug 115 inserted into dummy chamber 105, e.g., forced through slot 107. Tab 109 serves an orientation purpose. Encasement 100 should be curved to place tab 109 at the inside of the circlet. If encasement 100 is curved so as to place tab 109 at the outside of the circlet, encasement 100 will not fit inside drum base 34 for reason that the effective diameter of the circlet will be too great.

ENCASEMENT MOUNT AND USE STRUCTURE

The circlet form encasement 100 is sized to fit in drum base 34 adjacent cylindrical wall 61 provided tab 109 is at the open or rear face of drum base 34. If the user attempts to insert encasement 100 so that tab 109 will be adjacent the forward drum wall 63, tab 109 would interfere with structure at the inside of drum base 34 and the encasement will not fit into the drum base 34.

Inside of drum base 34, near the top thereof (see FIGS. 10, 11, 14, and 15) are formed a pair of arcuate guide portions 73 and 75, one on each side of the center line 200 of drum base 34. Guides 73 and 75 upstand from the inside face of front wall 63. If such is desired, the accurate guides 73 and 75 may be extended at their bottom ends into nearly a full circle guide portion. As may be seen in FIG. 3, the guides 73, 75 do not extend the full depth of circular sidewall 61, leaving a gap adjacent cover 31 into which the pin 37 on cover 31 extends.

Together with sidewall 61 guides 73 and 75 create an annular channel into which the medicament encasement 100 fits (see FIG. 10) except for a small overhang portion in the gap beyond the terminius of guides 73, 75. Orienting tab 109 becomes located in the above mentioned gap or free space adjacent cover 31, as is the stop element pin 37, which upstands from the inside of cover 31. Guide 75 has a tab 75' at its end to indicate where to place tab 109 (see FIG. 10), as the start position for encasement 100. Tab 75' may also serve as a stop element. Desirably, an indicator arrow 77 or equivalent indicia is formed on guide 75 or wall 63, to advise the user of the start position for loading medicament encasements into the implant applicator. FIG. 10 illustrates exactly where to position dummy chamber 105 and tab 109 when encasement 100 is loaded into the implant applicator.

A curved detent spring 79 fills the gap between guides 73, 75 (see FIGS. 10, 14, 15). Spring ends 81, 83 are mounted in channels provided for that purpose in posts 84 and 85 which respectively underlie and form part of guides 73, 75. The curved surface 87 on spring 79 contains a recess 87 at the intersection of drum axis line 200 and the central axis for needle 14 and impeller 22, which recess provides a seat for a chamber 102 indexing that chamber with impeller 22, so that impeller 22 can pass through the indexed chamber to expel the chamber contents 110 into, then through needle 14.

Clockwise rotation of medicament encasement 100 on guides 73, 75, the direction indicated on FIG. 10 is facilitated modestly by displacement of spring 79 to the left of center line 200 in the mode herein illustrated.

Figure 11:
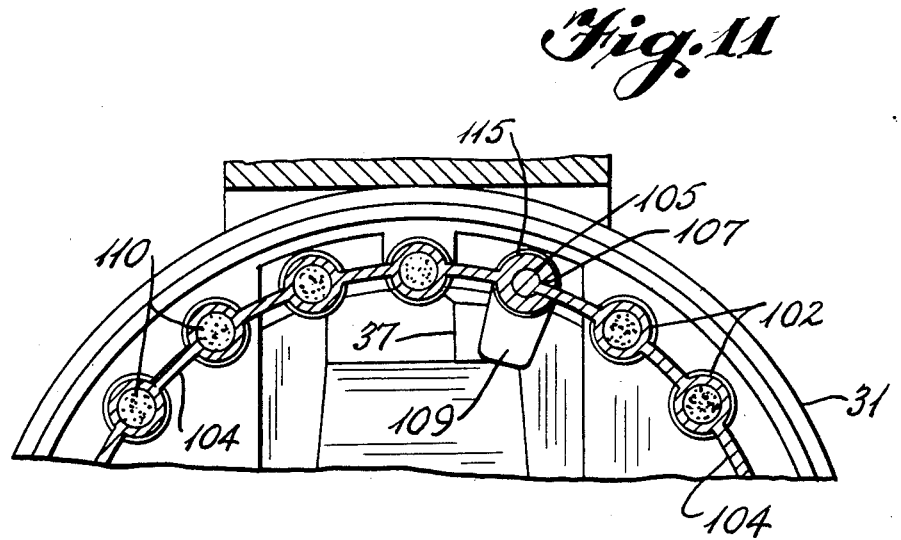
FIG. 11 is a partial section taken along line 12—12 of FIG. 3 for a loaded implant applicator.

Once the user has the circled encasement 100 inserted into implanter with dummy chamber 105 lined up to arrow 77, the chamber 102 adjacent to the dummy chamber 105 will seat in recess 87, as may be seen in FIGS. 10 and 11, locating dummy chamber 105 as the last chamber of encasement 100 to be indexed in recess 87.

Since insertion of encasement 100 into the implant applicator can be done only when members 30 and 34 have been pivoted apart on hinge pin 40 as shown in FIG. 2 providing access to the inside of drum base 34, pin 37 inside cover 31 has been swung away from drum base 34. Pin 37 plays no role in loading and unloading of the implant applicator. However, when hub 30 and drum base 34 are pivoted back and locked together in the use position of the implant applicator, pin 37 becomes located adjacent tab 109 between dummy chamber 105 and the chamber 102 adjacent thereto indexed on spring recess 87; see FIG. 11. Tab 75' is also in that locale; see FIG. 10, and if desired, together with or instead of pin 37, tab 75' may be employed for the stop function hereinafter described.

Clockwise movement of encasement 100 will shift each chamber 102 in succession onto the recess 87 of spring 79 until dummy chamber 105 approaches the indexed position, at which time tab 109 on medicament 100 is stopped by pin 37 (see FIG. 11). The encasement 100 can no longer be rotated. Preferably, the relative size and positions of tab 109 and pin 37 will allow the last chamber 102 to move off recess 87, but prevent indexing thereon of dummy chamber 105. The dummy chamber is filled by the non-expellable plug 115 in any event. Thus, the user cannot avoid recognizing when medicament encasement 100 has been emptied. Sheer inability to employ the applicator would advise the user that the applicator requires a fresh encasement.

Movement of encasement 100 chamber by chamber inside of the implant applicator is done when plunger 22 is retracted fully. At the left side of cylindrical wall 61 in the view of FIG. 10, may be seen the slot 130 wherein actuator 135 is deposed, seated in grooves provided in drum side wall 61 for that purpose. Actuator 135 may be a unitary molded object, e.g., from polyethylene. A push-pull nose 133 on the actuator extends through slot 130 to the outside of wall 61. The main body of actuator 135 is an arcuate portion that rides inside the side wall 61 of drum base 34 and follows the general contour of wall 61. That portion of wall 61 adjacent main body 135 is stepped outward to allow the actuator 135 to follow the wall contour as is illustrated in FIGS. 1 and 10. The main body of actuator 135 terminates in pusher finger 94. Finger 94 curves radially inward from the main body of actuator 135, to a terminus point near the juncture of a web section 104 with a chamber 102. The curvature of and normal position of finger 94 provides clearance for proper insertion of encasement 100 into drum base 34.

The length of travel allowed for actuator nose 133 in slot 130 corresponds to the spacing between adjacent chambers 102 of encasement 100. Thus, when nose 133 is resting at the base end of slot 130, as would be the situation when a fresh encasement has been loaded properly with arrow 77 lined up to the dummy chamber 105. The first chamber 102 is indexed in recess 87. Then, after discharge of the implant pellet medicament contents from the first chamber 102 followed by full retraction of plunger 22, which locates the plunger end clear of the chamber 102, as shown by FIG. 3, the user advances encasement 100 one chamber by pushing nose 133 from the base of slot 130 to the head thereof. This movement causes finger 94 to push encasement 100 a like distance, shifting the first medicament chamber 102 off spring detent 87, and the next chamber 102 on to recess 87 in its place, thereby indexing the next succeeding chamber 102 to plunger 22 and the bore of needle 14. Nose 133 may be pushed back before or after the contents of the indexed chamber 102 are expelled therefrom.

When nose 133 is retracted to the base of slot 130, as it must be before the encasement 100 can be advanced further, finger 94 deflects radically outward riding up and back over the next in line encasement chamber 102, then snaps back into its normal curvature and to terminate adjacent the juncture of web and chamber. The frictional drag during such reverse movement by finger 94 is insufficient to back the indexed encasement chamber 102 off spring recess 87. Accordingly, encasement 100 does not shift during the reverse movement of actuator 135. Desirably, stop 37 contacts encasement tab 109 before full indexing of dummy chamber 105 on spring recess 87 can occur. Further movement of finger 94 is stopped leaving the actuator nose 133 only partway along slot 135. Inability to shift the encasement 100 into an indexed position is used to advise the user that the implant applicator must be reloaded.

We claim:

1. A pistol-like medicament implanter comprising:
   (a) a hollow needle and a plunger in axial alignment, said plunger being movable into said hollow needle;
   (b) storage means for at least one medicament implant dosage unit interposed between needle and plunger, such dosage unit being disposed in a pass-through chamber indexed in line with needle and plunger whereby said plunger may travel through the indexed dosage unit chamber to expel the medicament therefrom; and
   (c) a trigger means and a plunger means operatively connected so that when said trigger means is pulled, said plunger advances through said chamber into the bore of said needle expelling thereby the implant dosage unit therefrom, and thereafter retracts when said trigger means is released;
   (d) the connection between trigger means and plunger means being an endless belt mounted between and interengaged with a drive gear driven by said trigger means and an idler sprocket, the plunger being disposed above said endless belt, riding thereon and being secured thereto, whereby said plunger is advanced and retracted through the movement of said endless belt around the drive gear upon pulling and retracting of said trigger means.

2. The implanter device of claim 1 wherein said endless belt is resilient.

3. The implanter device of claim 1 wherein said storage means comprises:
   (a) a drum interposed between needle and plunger, said drum being adapted to contain therein adjacent the drum periphery an encasement containing a multiplicity of medicament implant dosage units, said encasement being formed by a multiplicity of equally spaced apart parallel chambers and web sections connecting adjacent chambers, each chamber being adapted to contain one dosage unit of medicament implant therein;

(b) an index means inside said drum for indexing one chamber of said encasement in axial alignment with needle and plunger and means on said drum for shifting said chambers successively to said index means.

* * * * *